United States Patent [19]

Hughes et al.

[11] B 4,005,078

[45] Jan. 25, 1977

[54] DITHIOKETAL DERIVATIVES OF 13-POLYCARBONALKYLGON-4-EN-3-ONES

[75] Inventors: Gordon Alan Hughes, Haverford; Herchel Smith, Wayne, both of Pa.

[73] Assignee: Herchel Smith, Bryn Mawr, Pa.

[22] Filed: June 29, 1966

[21] Appl. No.: 561,365

[44] Published under the second Trial Voluntary Protest Program on April 13, 1976 as document No. B 561,365.

Related U.S. Application Data

[63] Continuation-in-part of Ser. Nos. 228,384, Oct. 4, 1962, Pat. No. 3,850,911, Ser. No. 337,823, Jan. 15, 1964, and Ser. No. 388,820, Aug. 11, 1964.

[52] U.S. Cl. .................................... 260/239.5
[51] Int. Cl.$^2$ ............................... C07J 33/00
[58] Field of Search ........................................
/Machine Searched Steroids

[56] References Cited

UNITED STATES PATENTS 3,850,911  11/1974  Hughes et al. ............... 260/397.4

*Primary Examiner*—Elbert L. Roberts
*Attorney, Agent, or Firm*—Gordon W. Hueschen; Vito Victor Bellino

[57] ABSTRACT

Novel 3-thioketals of 13-polycarbonalkyl-17-ethynyl-17-hydroxygon-4-ene and 13-polycarbonalkyl-17-chlorethynyl-17-hydroxygon-4-ene, with improved separation of activities, i.e. maximizing progestational and minimizing androgenic action, are prepared from the corresponding 3-carbonyl compounds by treatment with dithioethylene ketal in the presence of an acid catalyst.

5 Claims, No Drawings

DITHIOKETAL DERIVATIVES OF 13-POLYCARBONALKYLGON-4-EN-3-ONES

This application is a continuation-in-part of Ser. No. 228,384 filed Oct. 4, 1962, now U.S. Pat. No. 3,850,911, issued Nov. 26, 1974, Ser. No. 337,823 filed Jan. 15, 1964 and Ser. No. 388,820 filed Aug. 11, 1964.

This invention relates to compositions of matter classified in the art of chemistry as substituted unsaturated gonane derivatives.

The invention sought to be patented in a principal composition aspect is described as residing in the concept of a 17α-ethynyl- or 17α-chloroethynyl-17β-hydroxygon-4-ene-3-ketal, having an alkyl group containing two to four carbons at the 13-position and the acetate ester thereof.

The tangible embodiments of said principal composition aspect possess the inherent general physical properties of being high melting crystalline solids, substantially insoluble in water and generally soluble in polar solvents such as dimethylacetamide. Examination of compounds produced according to the hereinafter described procedures reveals, upon ultraviolet and infrared spectrographic analysis, spectral data supporting the molecular structures herein set forth. Thus, the disappearance in the infrared spectrum of the conjugated ketone peak at 6 μ is evident. The aforementioned physical characteristics, taken together with the nature of the starting materials, the mode of synthesis, and the elemental analysis, confirm the structure of the compositions sought to be patented.

The tangible embodiments of said principal composition aspect possess the use characteristic of exerting varying hormonal effects in animals as evidenced by pharmacological evaluation according to standard test procedures, and in particular the compositions of the invention possess a separation of hormonal activities wherein their progestational effect is maximized and androgenic effect minimized.

The manner of making the compositions of the invention will now be generally described so as to enable a person skilled in the art of chemistry to make and use the same, as follows:

The reactions utilized in preparation of the compositions of the invention are illustrated for a specific embodiment thereof in the following schematic representation where the compounds are assigned Roman numerals for identification:

Route A

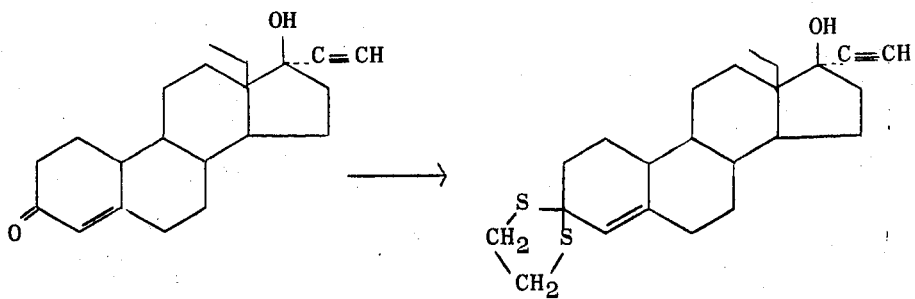

I    II

Route B

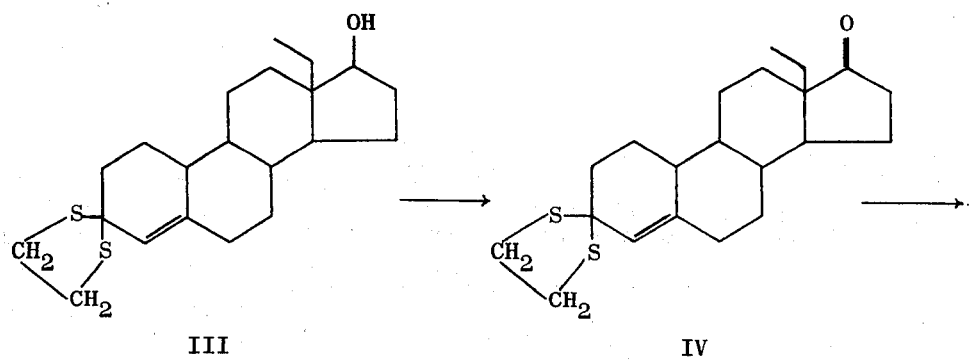

III    IV

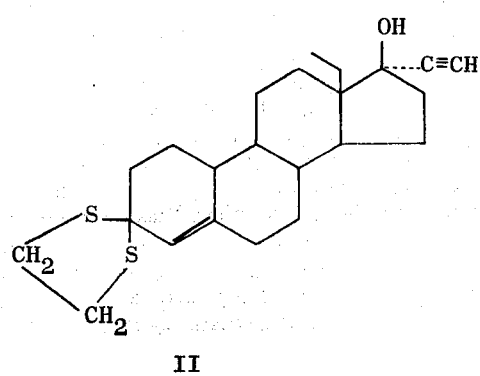

II

Referring now to Route A, the preparation of the 13-polycarbon-17-ethynyl-gon-4-en-3-ones (I) used as starting materials is described in the literature by Smith, H. et al. Jour. Chem. Soc. (London) 1964, 4472. Thioketalizing by reaction with ethane 1,2-dithiol in a solvent, preferably methanol, and in the presence of an acid catalyst, such as boron trifluoride etherate, produces the desired 3-thioketal derivative (II). Alternatively referring to Route A, the 3-thioketal of the 13-polycarbon-17-hydroxy-gon-4-en-3-ol (III) may be prepared as described above, the dithioketal alcohol can be oxidized under Oppenauer oxidation conditions to produce the corresponding 3-ketone IV, which on reaction with lithium acetylide gives the 3-thioketal II, of the invention. The latter can be converted to the 17-acetate ester by heating with a mixture of acetic acid anhydride and acetyl chloride in pyridine.

It will be apparent to one skilled in the art of chemistry that the 17-chloroethynyl compositions of the invention can be prepared by procedures analogous to those hereinbefore disclosed for the 17-ethynyl compositions. It will also be apparent to one skilled in the art that the above described procedures also may be utilized to prepare the embodiments of the compositions of the invention wherein the 13-alkyl group contains three or four carbon atoms, i.e., 13-propyl, 13-isopropyl, 13-butyl, etc. Similarly the 17-hydroxy can be esterified as for example, the acetate ester. The specific embodiments of the invention having the hereinbefore stated variations are qualitatively the full equivalents of the invention as specifically described in the use aspect of the invention although perhaps differing in degree of activity.

While the tetracyclic compounds in the specification and the appended examples are named either without regard to configuration, or to describe the configuration corresponding to that of the natural steroid, it is to be understood, the product of the given manipulative procedures is a racemic mixture which contains the compound corresponding to the natural steroid and its enantiomorph if the starting compound was a racemic mixture. However, if the starting compound is a particular enantiomorph, the final product also has the same enantiomorphic configuration.

When employed in the applied use characteristic of exerting qualitatively varying hormonal effects, the products of the invention are administered in pharmaceutical forms known to those skilled in the art of pharmacy. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders the carrier is a finely divided solid which is in admixture with the finely divided active compound. In the tablets the compound is mixed with a carrier having the necessary binding properties in suitable proportions and compacted in the shape and size desired. The powders and tablets preferably contain from 5 or 10 to 99% of the active ingredient. Suitable solid carriers are magnesium carbonate, magnesium stearate, talc, sugar, lactose, pectin, dextrin, starch, gelatin, tracanth, methylcellulose, sodium carboxymethylcellulose, low melting wax, and cocoa butter. Tablets, powders, cachets and capsules can be used for oral administration, and can be incorporated into formulations to obtain delayed or sustained release effects.

Liquid form preparations include solutions, suspensions, and emulsions. The compounds are insoluble in water, but can be dissolved in aqueous-organic solvent mixtures that are non-toxic in the amounts used. As an example may be mentioned water-propylene glycol solutions for parenteral injection. Liquid preparations can also be formulated in solution, in aqueous polyethyleneglycol. Aqueous suspensions suitable for oral use can be made by dispersing the finely divided compound in water with viscous material, such as natural or synthetic gums, resins, etc., for example, gum arabic, ion-exchange resins, methylcellulose, sodium carboxymethyl-cellulose, and other known suspending agents.

The quantity of compound in a unit dosage form may be adjusted from less than 1 mg. to 100 mg. (generally within the range of 2.5 to 25 mg.) and the effective dosage depends upon the severity of the condition being treated, the stage, the individual case, and the compound, and will be determined by an attending physician. Generally, a dosage range of from 0.25 to about 15 mg. per kg. of body weight per day constitutes the overall range.

The following examples illustrate the best mode contemplated by the inventors of carrying out their invention:

EXAMPLE 1

13β-Ethyl-17α-ethynyl-3,3-ethylenedithiogon-4-en-17β-ol

Treat 13β-ethyl-17α-ethynyl-17β-hydroxygon-4-en-3-one (1.0 g.) in methanol (30 cc.) with ethanedithiol (0.5 cc.) and boron trifluoride etherate (0.5 cc.) at 20° for 15 minutes. Dilute with water and extract with chloroform. Wash, dry and evaporate the organic solution, crystallize the residue by adding methanol and recrystallize from methanol containing a little acetone to obtain the title compound (0.44 g.); m.p. 172°–174°; infrared absorption peaks at 2.97, 3.45 $\mu$.

Analysis for $C_{23}H_{32}O_2S$: Calculated: C, 71.1; H, 8.3; S, 16.5. Found: C, 70.9; H, 8.0; S, 15.9.

EXAMPLE 2

13β-Ethyl-17α-ethynyl-3,3-ethylenedithiogon-4-en-17β-ol

Treat 13β-ethyl-17β-hydroxygon-4-en-3-one (0.47 g.) in methanol (5.0 cc.) and ethanedithiol (0.25 cc.) with boron trifluoride etherate (0.25 cc.) and allow the mixture to stand at 25° for 15 minutes, then cool to 0° and filter. Wash the residue with a little cold methanol and dry to obtain 13β-ethyl-3,3-ethylenedithiogon-4-en-17β-ol (0.38 g.), m.p. 167°–169°. Reflux 13β-ethyl-3,3-ethylenedithiogon-4-en-17β-ol (0.38 g.) in toluene (40 cc.) and cyclohexanone (5.0 cc.) containing aluminum isopropoxide (0.5 g.) and reflux for 3 hours in an atmosphere of nitrogen. Add water (2.0 cc.) to the cooled solution followed by anhydrous sodium sulphate. Filter, evaporate the filtrate and dissolve the crude residue in freshly distilled dimethylacetamide (15 cc.) saturated with acetylene and add lithium acetylide-ethyl-enediamine complex (1.0 g.). Stir in an atmosphere of acetylene for 4 hours, pour onto ice and extract with ether. Wash, dry and evaporate the ethereal solution and dissolve the residue in a little ether-benzene and filter through a column of neutral alumina. Evaporate the eluate and recrystallize the residue from methanol to obtain the title compound.

EXAMPLE 3

13β-Ethyl-17α-ethynyl-17β-acetoxy-3,3-ethylenedithiogon-4-ene

Treat 13β-ethyl-17α-ethynyl-17β-acetoxygon-4-en-3-one (1.0 g.) as described in Example 1 to obtain the title compound.

EXAMPLE 4

13β-Ethyl-17α-chloroethynyl-17β-hydroxy-3,3-ethylenedithiogon-4-ene

Treat 13β-ethyl-17α-chloroethynyl-17β-hydroxy-gon-4-en-3-one (2.0 g.) in methanol (35 cc.) with ethanedithiol (1.0 cc.) and boron trifluoride etherate (1.0 cc.) and allow the mixture to stand at 20° for 15 minutes. Cool to 0°, filter the precipitate and recrystallize from chloroform-methanol to obtain the title compound (1.66 g.), m.p. 202°–205°; infrared absorption peaks at 2.97, 3.44, 3.52, 4.54 μ.

Analysis for $C_{23}H_{31}OClS_2$:
Calculated: C, 65.3; H, 7.4; Cl, 8.4; S, 15.1.
Found: C, 65.0; H, 7.1; Cl 8.7; S, 15.3.

EXAMPLE 5

13β-Ethyl-17α-chloroethynyl-17β-acetoxy-3,3-ethylenedithiogon-4-ene

Treat 13β-ethyl-17α-chloroethynyl-17β-acetoxygon-4-en-3-one (1.0 g.) in methanol with ethanedithiol and boron trifluoride etherate as described in Example 1 to obtain the title compound.

The subject matter which the applicants regard as their invention is particularly pointed out and distinctly claimed as follows:

1. The composition of matter selected from the group consisting of 17-ethynyl-17β-hydroxy-gon-4-en-3-thioketal having an alkyl group containing 2 to 4 carbons at the 13-position, 17-chloroethynyl-17β-hydroxy-gon-4-en-3-thioketal having an alkyl group containing 2 to 4 carbons at the 13-position, and the acetate esters thereof.

2. A compound of claim 1 which is 13β-ethyl-17α-ethynyl-3,3-ethylenedithiogon-4-en-17β-ol.

3. A compound of claim 1 which is 13β-ethyl-17α-ethynyl-17β-acetoxy-3,3-ethylenedithiogon-4-ene.

4. A compound of claim 1 which is 13β-ethyl-17α-chloro-ethyl-17β-hydroxy-3,3-ethylenedithiogon-4-ene.

5. A compound of claim 1 which is 13β-ethyl-17α-chloro-ethynyl-17β-acetoxy-3,3-ethylenedithiogon-4-ene.

* * * * *